(12) United States Patent
Kondo (10) Patent No.: US 9,618,493 B2
(45) Date of Patent: Apr. 11, 2017

(54) SUBSTRATE PROCESSING APPARATUS AND METHOD FOR DETECTING AN ABNORMALITY OF AN OZONE GAS CONCENTRATION

(71) Applicant: Tokyo Electron Limited, Tokyo (JP)

(72) Inventor: Masaki Kondo, Miyagi (JP)

(73) Assignee: Tokyo Electron Limited, Tokyo (JP)

( * ) Notice: Subject to any disclaimer, the term of this patent is extended or adjusted under 35 U.S.C. 154(b) by 183 days.

(21) Appl. No.: 14/565,747

(22) Filed: Dec. 10, 2014

(65) Prior Publication Data

US 2015/0168363 A1 Jun. 18, 2015

(30) Foreign Application Priority Data

Dec. 18, 2013 (JP) .................................. 2013-261673

(51) Int. Cl.
 *G01N 33/00* (2006.01)
(52) U.S. Cl.
 CPC .............................. *G01N 33/0039* (2013.01)
(58) Field of Classification Search
 CPC .................................................. G01N 33/0039
 See application file for complete search history.

(56) References Cited

U.S. PATENT DOCUMENTS

| | | | | |
|---|---|---|---|---|
| 6,511,924 B2* | 1/2003 | Mukai | ................... | C23C 16/401 257/E21.279 |
| 6,616,773 B1* | 9/2003 | Kuzumoto | ................ | B08B 7/00 134/1.3 |
| 2004/0002224 A1* | 1/2004 | Chono | .............. | H01L 21/67253 438/714 |
| 2004/0069226 A1* | 4/2004 | Yoshida | ............ | H01L 21/67167 118/715 |
| 2006/0240677 A1* | 10/2006 | Horii | ................. | H01L 21/02238 438/770 |
| 2013/0092084 A1* | 4/2013 | Shao | ....................... | C23C 16/52 118/712 |
| 2014/0156090 A1* | 6/2014 | Krishnan | ............. | G05D 7/0617 700/282 |
| 2015/0021162 A1* | 1/2015 | Wada | ...................... | C01B 13/11 204/176 |

FOREIGN PATENT DOCUMENTS

JP 2011-005360 1/2011

* cited by examiner

*Primary Examiner* — Francis Gray
(74) *Attorney, Agent, or Firm* — IPUSA, PLLC (57) ABSTRACT

A substrate processing apparatus is provided that includes an ozonizer for generating ozone gas and an ozone sensor for detecting an ozone gas concentration. The substrate processing apparatus processes a substrate by using the ozone gas supplied from the ozonizer. The substrate processing apparatus includes a monitor unit for monitoring the ozone gas concentration detected by the ozone sensor and a control unit for detecting an abnormality of the ozone gas concentration based on the monitored ozone gas concentration and the monitored discharge power.

6 Claims, 5 Drawing Sheets

SUBSTRATE PROCESSING APPARATUS AND METHOD FOR DETECTING AN ABNORMALITY OF AN OZONE GAS CONCENTRATION

CROSS-REFERENCE TO RELATED APPLICATIONS

This patent application is based upon and claims the benefit of priority of Japanese Patent Application No. 2013-261673, filed on Dec. 18, 2013, the entire contents of which are incorporated herein by reference.

BACKGROUND OF THE INVENTION

1. Field of the Invention

The present invention relates to a substrate processing apparatus and a method for detecting an abnormality of an ozone gas concentration.

2. Description of the Related Art

As disclosed in Japanese Laid-Open Patent Application Publication No. 2011-5360, a technique is known of determining a state of a device for generating ozone gas or a device for decomposing ozone gas by using an ozone concentration detected by an ozone sensor. In Japanese Laid-Open Patent Application Publication No. 2011-5360, whether the device for decomposing ozone gas comes to the end of its life is determined by detecting an ozone gas concentration supplied to the device by the ozone sensor and by determining whether a proper amount of ozone gas is supplied to the device.

However, in Japanese Laid-Open Patent Application Publication No. 2011-5360, the determination is wrong when the ozone sensor does not work normally and the detected ozone gas concentration is not a normal value, which causes trouble. In particular, regular maintenance of the ozone sensor has to be performed, for example, once a day, which is so frequent that actual implementation of the maintenance is often difficult.

SUMMARY OF THE INVENTION

Accordingly, in response to the above discussed problems, one embodiment of the present invention aims to provide a substrate processing apparatus and a method for detecting an abnormality of an ozone concentration that can reliably supply ozone gas by detecting an abnormality of an ozone concentration.

According to one embodiment of the present invention, there is provided a substrate processing apparatus that includes an ozonizer for generating ozone gas and an ozone sensor for detecting an ozone gas concentration and processes a substrate by using the ozone gas supplied from the ozonizer. The substrate processing apparatus includes a monitor unit for monitoring the ozone gas concentration detected by the ozone sensor, a discharge power of the ozonizer, and a control unit configured to detect an abnormality of the ozone gas concentration based on the monitored ozone gas concentration and the monitored discharge power.

According to another embodiment of the present invention, there is provided a method for detecting an abnormality of an ozone gas concentration used in a substrate processing apparatus for processing a substrate by using an ozonizer for generating ozone gas. In the method, an ozone gas concentration detected by an ozone sensor of the ozone gas supplied from the substrate processing apparatus is monitored, and a discharge power of the ozonizer is monitored. An abnormality of the ozone gas concentration detected by the ozone sensor is detected based on the monitored ozone gas concentration and the monitored discharge power.

Additional objects and advantages of the embodiments are set forth in part in the description which follows, and in part will become obvious from the description.

DETAILED DESCRIPTION OF THE PREFERRED EMBODIMENTS

A description is given below of embodiments of the present invention, with reference to accompanying drawings. Note that elements having substantially the same functions or features may be given the same reference numerals and overlapping descriptions thereof may be omitted.

[Introduction]

In manufacture of semiconductor integrated circuits, when a plasma etching is performed on a substrate such as a semiconductor wafer (hereinafter, "wafer") or the like, radicals and ions generated in plasma goes around a bevel surface and a back surface of the wafer, and a polymer attaches to the bevel surface and the back surface. The attachments are called a bevel/backside polymer (Bevel/Backside Polymer, hereinafter "BSP"). The BSP is liable to affect the semiconductor integrated circuit. Therefore, a BSP removal device for removing the BSP by a heat treatment using laser and ozone gas is known.

In the BSP removal device, when a proper amount of ozone gas is not supplied thereinto, an etching rate when removing the BSP decreases. Therefore, an ozone gas concentration supplied into the BSP removal device is detected by an ozone gas sensor, and whether or not the proper amount of ozone gas is supplied into the BSP removal device is determined.

At this time, when the ozone sensor does not work normally, a wrong ozone gas concentration is detected. However, when using the ozone sensor, an offset operation needs to be performed regularly (e.g., once a day) to adjust the zero point. This regular maintenance is so frequent that maintaining the ozone sensor as described in the manual is frequently difficult.

The ozone sensor detects an attenuation rate of UV light from a UV lamp arranged above and below a quarts tube when a gas flows through the quartz tube. The ozone sensor measures an ozone gas concentration by utilizing a decrease in transmission of the UV light from the UV lamp when the ozone gas flows through the quartz tube. Hence, when the quartz tube becomes dim itself, the dimness causes an error of the ozone gas concentration detected by the ozone sensor.

When a detected value of the ozone gas concentration differs from the actual ozone gas concentration supplied into the BSP removal device, as discussed above, performance at the time of removing the BSP decreases. Therefore, an embodiment is given below of a substrate processing apparatus and a method for detecting an abnormality of an ozone gas concentration that can reliably detect an accurate ozone concentration.

The substrate processing apparatus according to the embodiment includes a whole apparatus that processes a substrate by using an ozonizer for generating ozone gas. To begin with, a description is given below of a BSP removal device that removes BSP attached to a back surface or a bevel surface of a wafer as an example of the substrate processing apparatus according to embodiments. After that, a description is given of a method for detecting an abnormality of an ozone gas concentration according to embodiments.

[Overall Configuration of BSP Removal Device]

Figure 1:
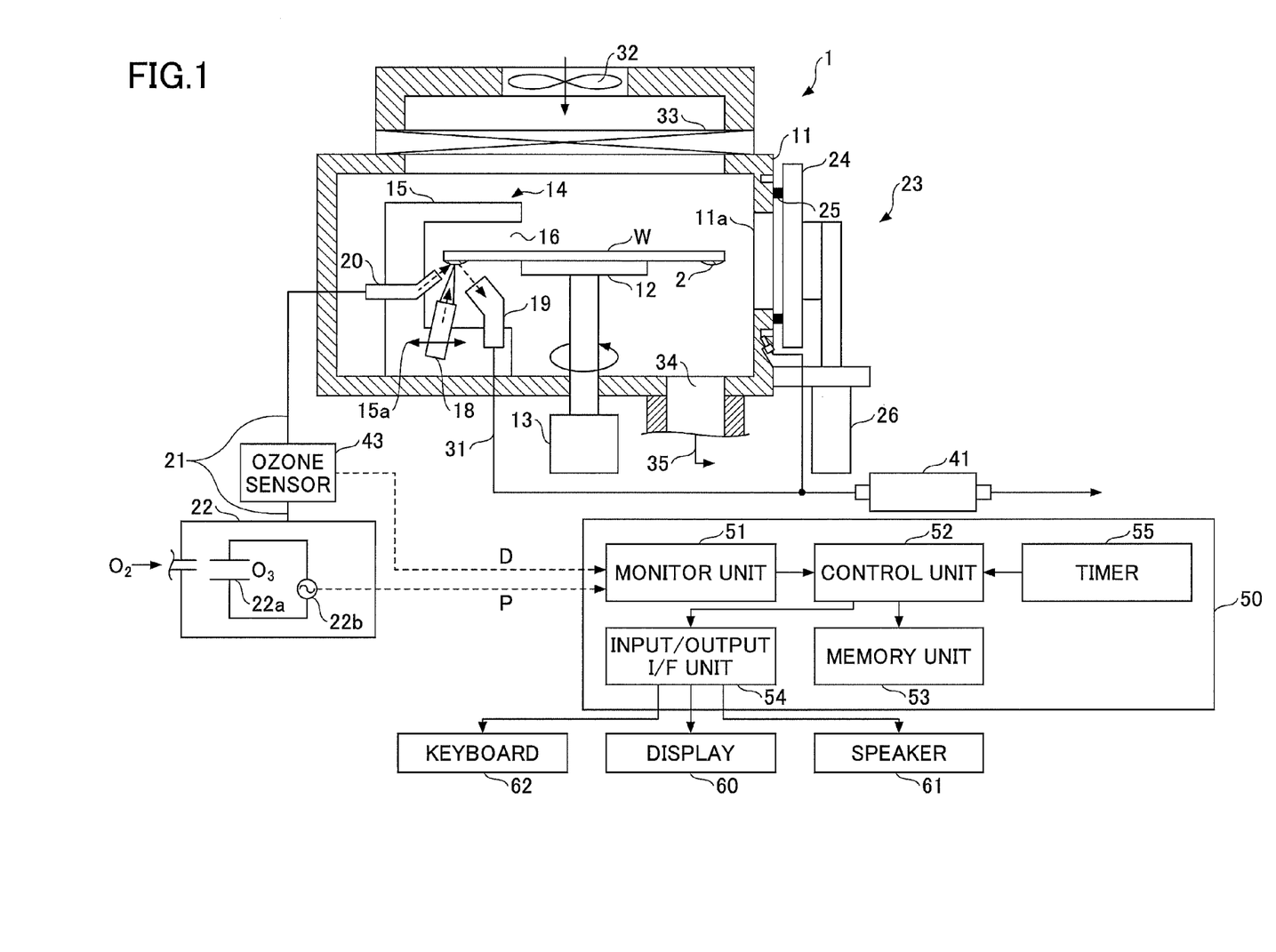
FIG. 1 is a diagram illustrating an example of an overall configuration of a BSP removal device according to an embodiment of the present invention.

To begin with, a description is given below of an overall configuration of a BSP removal device according to an embodiment with reference to FIG. 1. FIG. 1 illustrates an example of the overall configuration of the BSP removal device 1 according to the embodiment.

The BSP removal device 1 includes a chamber 11 that forms a container for containing a wafer W to which BSP 2 has been attached. A spin chuck 12 is provided inside the chamber 11 to hold the wafer W horizontally and rotatably. The spin chuck 12 is connected to a rotary motor 13 provided under the chamber 11. The spin chuck 12 is configured to rotate the wafer W suctioned and held by the spin chuck 12 by revolving in a state of holding the wafer W by, for example, vacuum suction.

Inside the chamber 11, a BSP removal unit 14 is provided in a position corresponding to a peripheral part of the wafer W. A main body 15 that constitutes the BSP removal unit 14 includes a cutout portion 16 so as to allow the peripheral part of the wafer W to pass therethrough while rotating. A laser irradiation head 18 to irradiate the BSP 2 attached to the wafer W with a laser beam is provided at a lower part 15a located below the cutout portion 16. The laser irradiation head 18 is configured to be movable in a radial direction of the wafer W along the lower part 15a of the main body 15. Moreover, an angle of the laser irradiation head 18 is changeable. This allows a laser irradiation position to be adjustable depending on an adhesion condition of the BSP 2. The main body 15 includes an ozone gas discharge nozzle 20 that discharges ozone gas to the BSP 2 and an ozone gas suction nozzle 19 that suctions almost 100 percent of ozone gas. The ozone gas discharge nozzle 20 is connected to an ozonizer 22 through a supply line (a pipe) 21 for supplying ozone gas. Ozone gas is output from the ozonizer 22, introduced into the chamber 11 through the supply line 21, and discharged from the ozone gas discharge nozzle 20. An exhaust pipe 31 that constitutes an exhaust flow passage for mainly evacuating ozone gas is connected to the ozone gas suction nozzle 19. The exhaust pipe 31 is connected to a factory oxide exhaust pipe (not illustrated in the drawings). An ozone killer 41 for decomposing ozone gas is connected to the exhaust pipe 31.

A fan 33 for taking air into the chamber 11 by suctioning the air and a filter 33 for removing particles in the air suctioned by the fan 32 are provided on the upper side of the chamber 11. An exhaust opening 34 is provided in a bottom part of the chamber 11. A down flow of cleaned air is formed inside the chamber 11 by taking the air into the chamber 11 through the filter 33 by the fan 32 and by evacuating the taken air from the exhaust opening 34. An exhaust pipe 35 is connected to the exhaust opening 34, and the exhaust pipe 35 is connected to the factory oxide exhaust pipe (not illustrated in the drawings).

A wafer carry-in/out opening 11a is provided in a side wall of the chamber 11, and the wafer carry-in/out opening 11a is openable and closeable by a gate valve 23. The gate valve 23 includes a valve element 24 and an air cylinder 26 for opening and closing the valve element 24. When closing the valve element 24, a gap between the valve element 24 and the chamber 11 is sealed by a seal ring 25.

An ozone sensor 43 is connected to any position between the supply line 21 and the ozone gas discharge nozzle 20, and detects an ozone gas concentration D of ozone gas supplied into the chamber 11. The ozone sensor 43 may be connected to the exhaust pipe 31. In this case, the ozone sensor 43 detects an ozone gas concentration of ozone gas evacuated from the chamber 11.

A form of the ozone sensor 43 is not limited as long as the ozone sensor 43 can detect an ozone concentration with a high degree of accuracy. As an example of the ozone sensor 43, a form specified by JIS (Japanese Industrial Standard) can be preferably used such as a form of determining the quantity of the ozone concentration by measuring absorbance of iodine ions liberated from a normal potassium iodide solution by oxidant, a form of determining the quantity of the ozone concentration by measuring absorbance of ozone in a ultraviolet light range and the like.

The BSP removal device 1 includes a control device 50. The control device 50 mainly controls each component of the BSP removal device 1. The control device 50 includes a monitor unit 51, a control unit 52, a memory unit 53, an input-output I/F (interface) unit 54 and a timer 55.

The monitor unit 51 monitors an ozone gas concentration D detected by the ozone sensor 43. More specifically, the monitor unit 51 receives an input of the ozone gas concentration D from the ozone sensor 43 regularly or irregularly and outputs the ozone gas concentration D to the control unit 52.

The monitor unit 51 also monitors discharge power P of the ozonizer 22. The ozonizer 22 supplies $O_2$ gas to a space between parallel plate electrodes 22a, converts the $O_2$ gas to $O_3$ gas, and outputs the $O_3$ gas. On this occasion, low-frequency electricity of about 25 kHz is supplied to the electrodes 22a. The monitor unit 51 receives an input of electrical power P output from the electrodes 22a within the ozonizer 22 regularly or irregularly and outputs the electrical power P to the control unit 52.

The control unit 52 includes a microprocessor. The control unit 52 is connected to the input-output I/F unit 54, and is further connected to a keyboard 62 to allow an operator to perform an input operation of a command and the like for managing the BSP removal device 1, and a display 60 and a speaker 61 for outputting information and the like through the input-output I/F unit 54. A memory unit 53 storing a control program for performing predetermined control or a process recipe is connected to the control unit 52. The process recipe is stored in a storage medium in the memory unit 53. The control unit 52 controls the BSP removal process by calling any process recipe from the memory unit 53 and executing the process recipe in accordance with an instruction or the like from the input-output I/F unit 54 as necessary.

The memory unit 53 preliminarily stores information showing a correlation between the ozone gas concentration and the discharge power (which is also hereinafter just called "correlated information"). The ozone gas concentration bears a proportional relationship to the discharge power. Hence, the memory unit 53 preliminarily stores a proportional expression thereof. The control unit 52 detects whether or not the ozone gas concentration detected by the ozone sensor 43 has an abnormality in accordance with the stored correlated information, based on the monitored ozone gas concentration D and the monitored discharge power P. A timer 55 measures operating time of the ozonizer 22.

Figure 3:
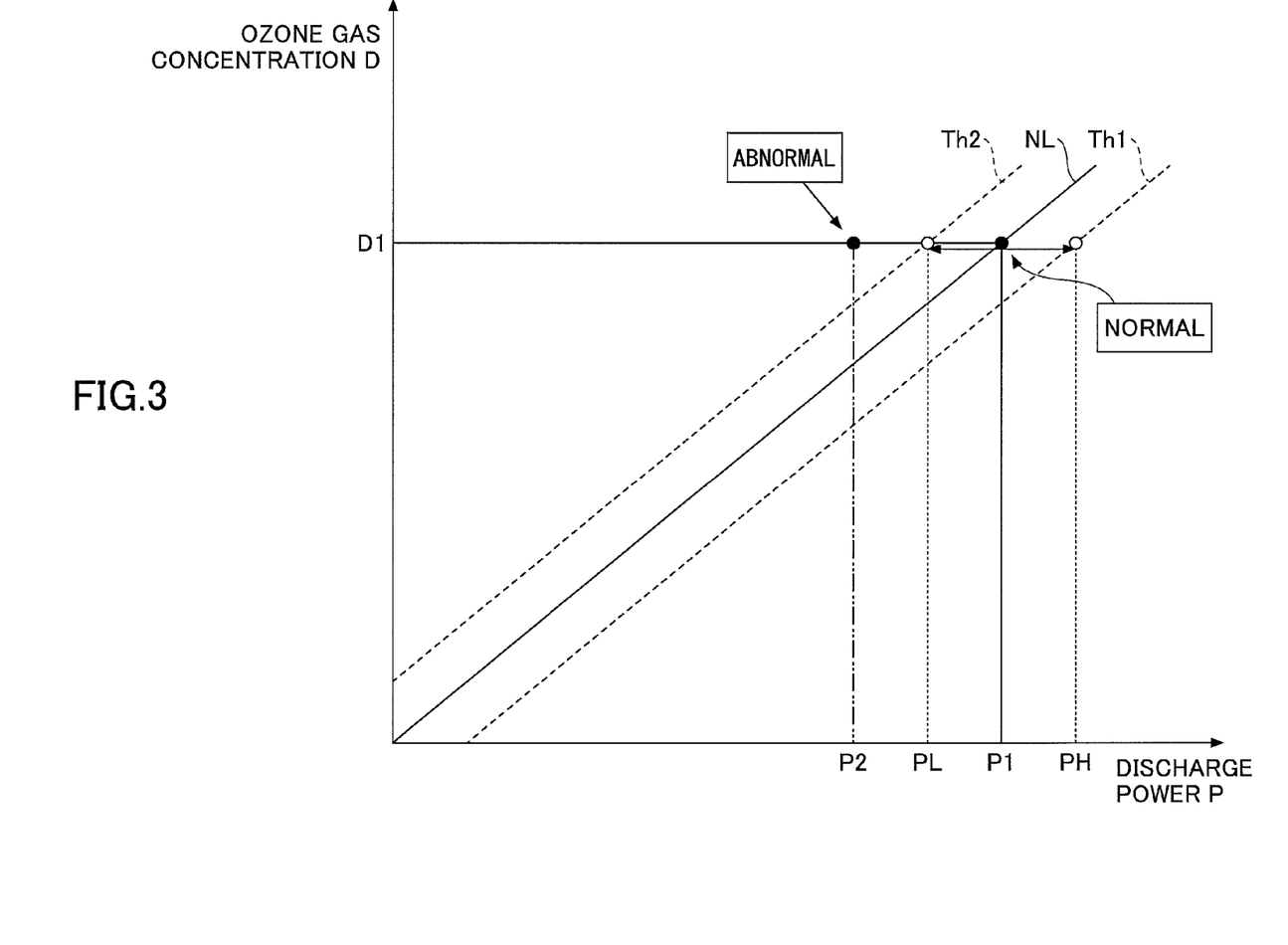
FIG. 3 is a chart illustrating an example of a graph illustrating a correlation between an ozone gas concentration and discharge power.

FIG. 3 is a chart illustrating an example of the correlated information showing the correlation between the ozone gas concentration and the discharge power stored in the memory unit 53 in a form of a graph. A straight line NL graphically illustrates a proportional expression of the correlation between the ozone gas concentration and the discharge power (ideal value) when the ozone sensor 43 is normal. Straight lines of the threshold Th1 and the threshold Th2 illustrate an acceptable range capable of determining that the ozone sensor 43 is normal. More specifically, a value of the monitored discharge power P corresponding to the monitored ozone gas concentration D ideally lies on the straight line NL, but is acceptable when the value is in a rage of the straight lines from the threshold Th1 to the threshold Th2. This prevents the process of detecting the abnormality of the ozone gas concentration from being too strict.

Accordingly, when the monitored ozone gas concentration D is "D1", the ozone gas concentration detected by the ozone sensor 43 is determined to be normal as long as the detected discharge power has any value in a range of PL to PH (range within the acceptable value), as well as the case of the monitored discharge power being P1. In contrast, when the ozone gas concentration D detected by the ozone sensor 43 is "D1" and the detected discharge power is out of the range of PL to PH, the ozone gas concentration detected by the ozone sensor 43 is determined to be abnormal. For example, when the detected discharge power is P2, the detected ozone gas concentration is determined to be abnormal.

The proportional expression showing the straight lines of the threshold Th1 and the threshold Th2 is preliminarily stored in the memory unit 53 with the proportional expression showing the straight line NL. The etching performed by the BSP removal device 1 has a point at which the etching rate sharply drops due to change of the ozone gas concentration. Therefore, the threshold Th1 and the threshold Th2 are preliminarily set at values showing acceptable maximum correlated information of the correlated information showing the correlation between the ozone gas concentration and the discharge power before the etching rate sharply drops due to the change of the ozone gas concentration.

The control unit 52 detects the abnormality of the ozone gas concentration according to the correlated information stored in the memory unit 53, based on the ozone gas concentration D and the discharge power P monitored by the monitor unit 51. More specifically, the control unit 52 detects the abnormality of the ozone gas concentration depending on the correlated information stored in the memory unit 53 when the monitored discharge power P corresponding to the monitored ozone gas concentration D is out of the predetermined range from the threshold Th1 to the threshold Th2.

The control unit 52 may display an alarm on the display 60 through the input-output I/F unit 54 when detecting the abnormality of the ozone gas concentration. Moreover, the control unit 52 may cause the speaker 61 to beep through the input-output I/F unit 54 when detecting the abnormality of the ozone gas concentration.

Referring to FIG. 1 again, in the BSP removal device 1 having such a configuration, to begin with, the valve element 24 of the gate valve 23 is opened, and a wafer W is carried into the chamber 11a through the carry-in/out opening 11a by a transfer arm which is not illustrated in the drawings and is suctioned on the spin chuck 12 by vacuum evacuation. Then, the valve element 24 of the gate valve 23 is closed and the chamber 11 is hermetically sealed.

Next, the spin chuck 12 is rotated by the rotary motor 13, thereby rotating the wafer W held on the spin chuck 12 by being suctioned. While rotating the wafer W in this manner, the BSP removal unit 14 irradiates the BSP 2 attached to the wafer W with a laser beam emitted from the laser irradiation head 18, blows ozone gas onto the BSP 2 from the ozone discharge nozzle 20, and suctions ozone gas by the ozone gas suction nozzle 19. This causes the BSP 2 to be removed by heat caused by the laser beam irradiation and oxidation by ozone gas. At this time, the irradiation head 18 is moved in a radial direction of the wafer W so as to irradiate a desired location with the laser beam, and the angle of the laser irradiation head 18 is adjusted. During the BSP removal process, ozone gas is supplied from the ozone gas discharge nozzle 20 and the supplied ozone gas is evacuated from the ozone gas suction nozzle 19 through the exhaust pipe 31 that forms the exhaust flow passage.

In the embodiment, the ozone sensor 43 detects the ozone gas concentration D sampled from the supply line 21 for supplying the ozone gas, and the monitor unit 51 monitors the ozone gas concentration D. Also, in the embodiment, the monitor unit 51 detects and monitors the discharge power P of the ozonizer 22.

The control unit 52 compares the ozone gas concentration D and the discharge power P monitored by the monitor unit 51 to the correlated information stored in the memory unit 53. When the monitored discharge power P corresponding to the monitored ozone gas concentration D is out of the predetermined range of the threshold Th1 to the threshold Th2, the control unit 52 detects that the monitored ozone gas concentration is abnormal and outputs an alarm. An operator that recognized the alarm stops the BSP removal device 1 and performs maintenance such as point correction (offset) of the ozone sensor 43 or the like.

The control device 50 includes a CPU (Central Processing Unit), a ROM (Read Only Memory), a RAM (Random Access Memory) and the like that are not illustrated in the drawings. A function of the control unit 52 is implemented by the CPU. A function of the memory unit 53 is implemented by the ROM or the RAM. The CPU controls supply of the low-frequency electricity, supply of ozone gas, irradiation of the laser beam and the like in accordance with the recipe stored in a memory area of the ROM and the like, and performs the BSP removal process. Moreover, the CPU detects the abnormality of the monitored ozone gas concentration depending on the correlated information stored in the memory area of the ROM and the like.

The function of the control unit 52 may be implemented by running software or by using hardware.

As discussed above, a description has been given of an example of the overall configuration of the BSP removal device 1 according to the embodiment of the present invention. Next, a description is given below of an example of a process of detecting an abnormality of an ozone gas concentration implemented by the control device 50 of the BSP removal device 1 with reference to FIG. 2.

[Process of Detecting Abnormality of Ozone Gas Concentration]

Figure 2:
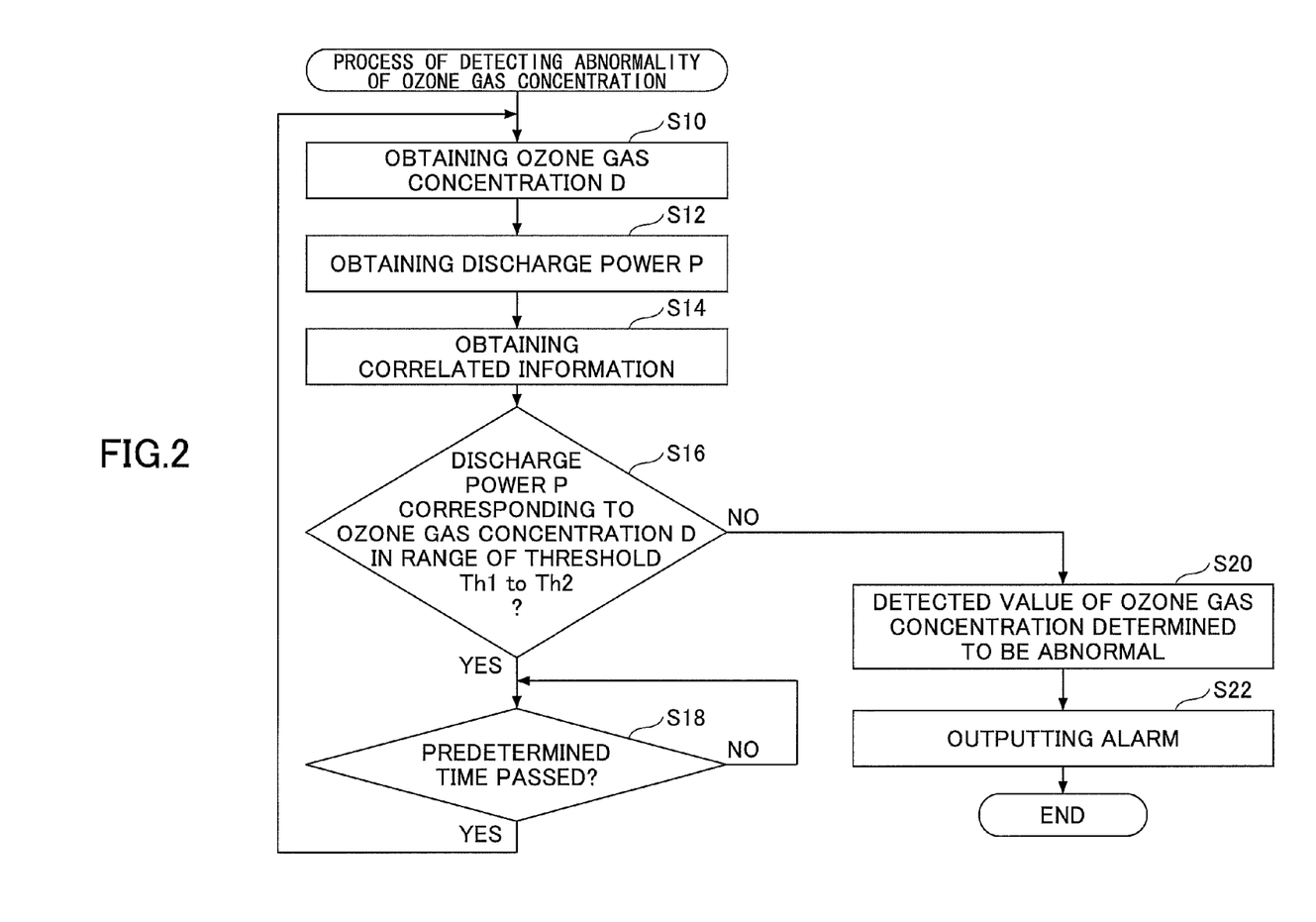
FIG. 2 is a flowchart illustrating an example of an abnormality detecting process of an ozone gas concentration according to an embodiment of the present invention.

When the process of detecting the abnormality of the ozone gas concentration in FIG. 2 starts, the control unit 52 obtains an ozone gas concentration D from the monitor unit 51 (step S10). Next, the control unit 52 obtains discharge power P from the monitor unit 51 (step S12). Here, obtaining timing and an obtaining order of steps S10 and S12 are not limited to this example.

Next, the control unit 52 obtains correlated information showing a proportional expression of a straight line NL and correlated information showing a proportional expression of thresholds Th1 and Th2 from the memory unit 53 (step S14). Subsequently, the control unit 52 determines whether the obtained discharge power P corresponding to the obtained ozone gas concentration D is in a range of the thresholds Th1 to Th2 (step S16). For example, in FIG. 3, it is determined whether the obtained discharge power P1 corresponding to the ozone gas concentration D1 is in the range of PL to PH.

When the discharge power P corresponding to the ozone gas concentration D is in the range of the thresholds Th1 to Th2, the control unit 52 detects that the monitored ozone gas concentration is normal. For example, in FIG. 3, when the obtained discharge power P corresponding to the obtained ozone gas concentration D1 is "P1", the control unit 52 detects that the monitored ozone gas concentration is normal. In this case, it is determined that the ozone sensor 43 operates normally, and that monitoring the ozone gas during the BSP removal process can be continued. Accordingly, after the elapse of a predetermined period of time (step S18), the process returns to step S10, and the control unit 52 performs the next abnormality detection process (steps S10 through S16) based on a new ozone gas concentration D and discharge power P.

In contrast, in step S16, when the discharge power P corresponding to the ozone gas concentration D is out of the range of thresholds Th1 to Th2, the control unit 52 detects that the monitored ozone gas concentration is abnormal (step S20). For example, in FIG. 3, when the obtained discharge power P corresponding to the obtained ozone gas concentration D1 is "P2", the control unit 52 detects that the monitored ozone gas concentration is abnormal. When detecting the abnormality, the control unit 52 performs control of outputting an alarm (step S22), and ends the process of detecting the abnormality of the ozone gas concentration. Displaying "maintenance (zero-point adjustment) of ozone sensor 43 is needed" on the display 60 or outputting a warning sound from the speaker 61 is taken as an example of the output alarm.

As discussed above, a description has been given of an example of the process of detecting the abnormality of the ozone gas concentration performed by the control device 50 of the ESP removal device 1 according to the embodiment of the present invention.

When the ozone sensor 43 does not normally operate, an ozone gas concentration different from the actual ozone gas concentration of the ozone gas actually supplied to the BSP removal device 1 is detected. In particular, because regular maintenance of the ozone sensor is frequent, for example, once a day, performing the maintenance as required is frequently difficult.

Therefore, the process of detecting the abnormality of the ozone gas concentration according to the embodiment monitors presence or absence of the abnormality of the ozone gas concentration from the detected value of the ozone sensor 43 and the discharge power of the ozonizer 22. Then, whether the ozone sensor 43 can accurately detect the ozone gas concentration is determined based on whether the correlation between the monitored ozone gas concentration and discharge power is in an acceptable range of the predetermined correlation between the ozone gas concentration and the discharge power. In this manner, whether or not the detection value of the ozone gas concentration detected by the ozone sensor 43 is normal can be determined.

This makes it possible to find the abnormality of the ozone sensor 43 in the early stage, and to encourage an operator to perform maintenance (zero-point adjustment) of the ozone sensor 43 and to promptly fix malfunction or derivation of zero point of the ozone sensor 43. Such a prompt action of an operator leads to achieve stable supply of the ozone gas, to prevent a decrease in processing performance of the BSP removal by the BSP removal device 1, and to avoid a lot defect.

[Modification]

A slope of the proportional expression of the ozone gas concentration and the discharge power may change depending on temporal change of the ozonizer 22. For example, the slope of the proportional expression of the ozone gas concentration and discharge power may decrease depending on the temporal change of the ozonizer 22.

In a modification of the embodiment described below, the memory unit 53 preliminarily stores a plurality of pieces of correlated information showing a correlation between the ozone gas concentration and the discharge power that change depending on operating time of the ozonizer 22. More specifically, the memory unit 53 preliminarily stores a plurality of proportional expressions showing correlations between the ozone gas concentration and the discharge power. The control unit 52 selects the correlated information showing the optimal correlation between the ozone gas concentration and the discharge power from the plurality pieces of correlated information stored in the memory unit 53 depending on the operating time of the ozonizer 22.

More specifically, the operating time of the ozonizer 22 is measured by the timer 55. The control unit 52 selects the most appropriate correlated information among the plurality pieces of correlated information stored in the memory unit 53, and detects the abnormality of the ozone gas concentration based on the selected correlated information. A description is given below of a process of selecting the correlated information from the plurality of pieces of correlated information showing the correlation of the ozone gas concentration and the discharge power with reference to FIG. 4.

[Process of Selecting Correlated Information]

Figure 4:
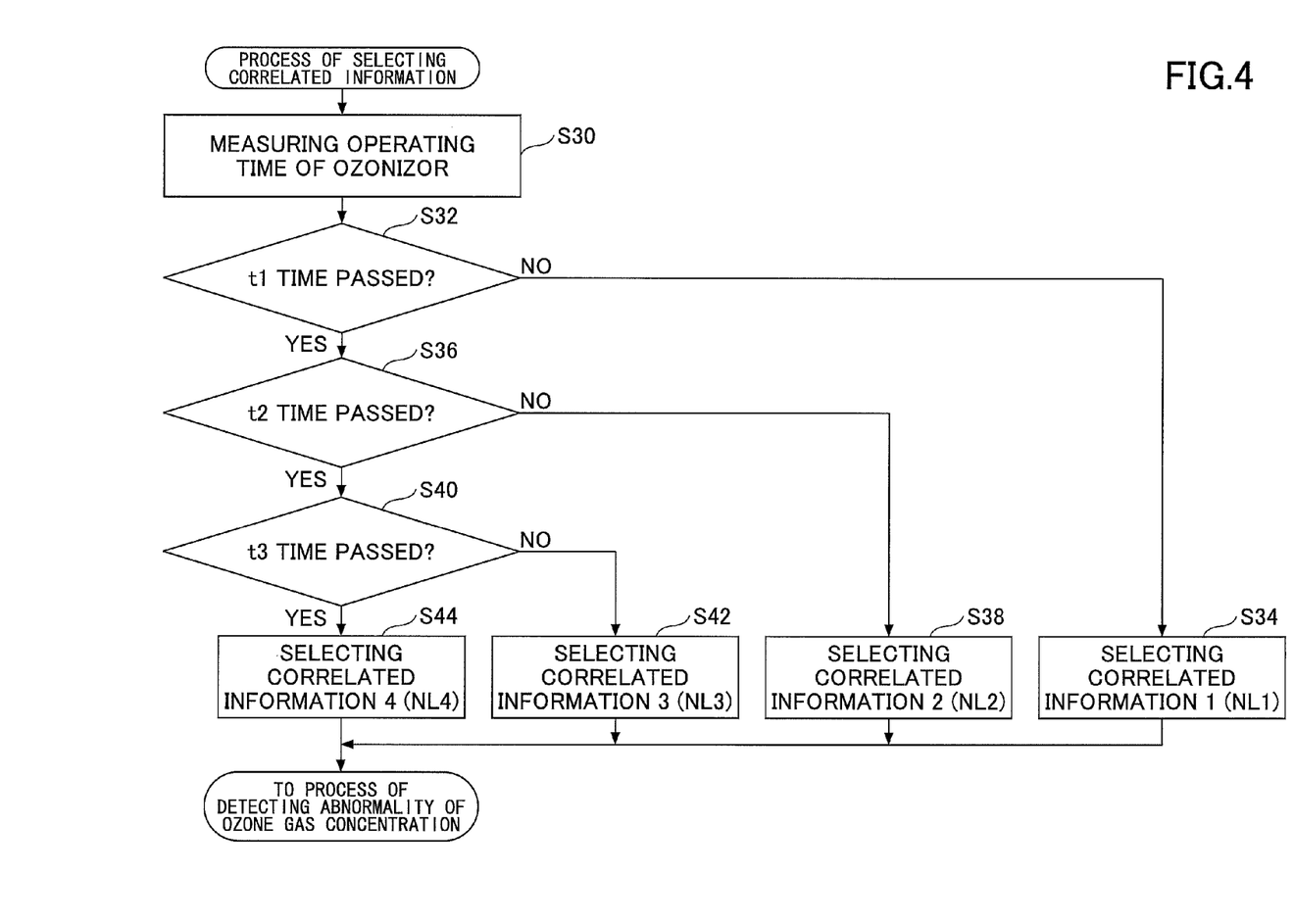
FIG. 4 is a flowchart illustrating an example of a selective process of correlated information according to an embodiment of the present invention.

FIG. 4 is a flowchart illustrating an example of a process of selecting the correlated information according to an embodiment.

When the process of selecting the correlated information in FIG. 4 starts, the control unit 52 obtains operating time of the ozonizer 22 measured by the timer 55 (step S30). The control unit 52 determines whether or not the operating time of the ozonizer 22 has passed over predetermined time t1 (step S32).

Figure 5:
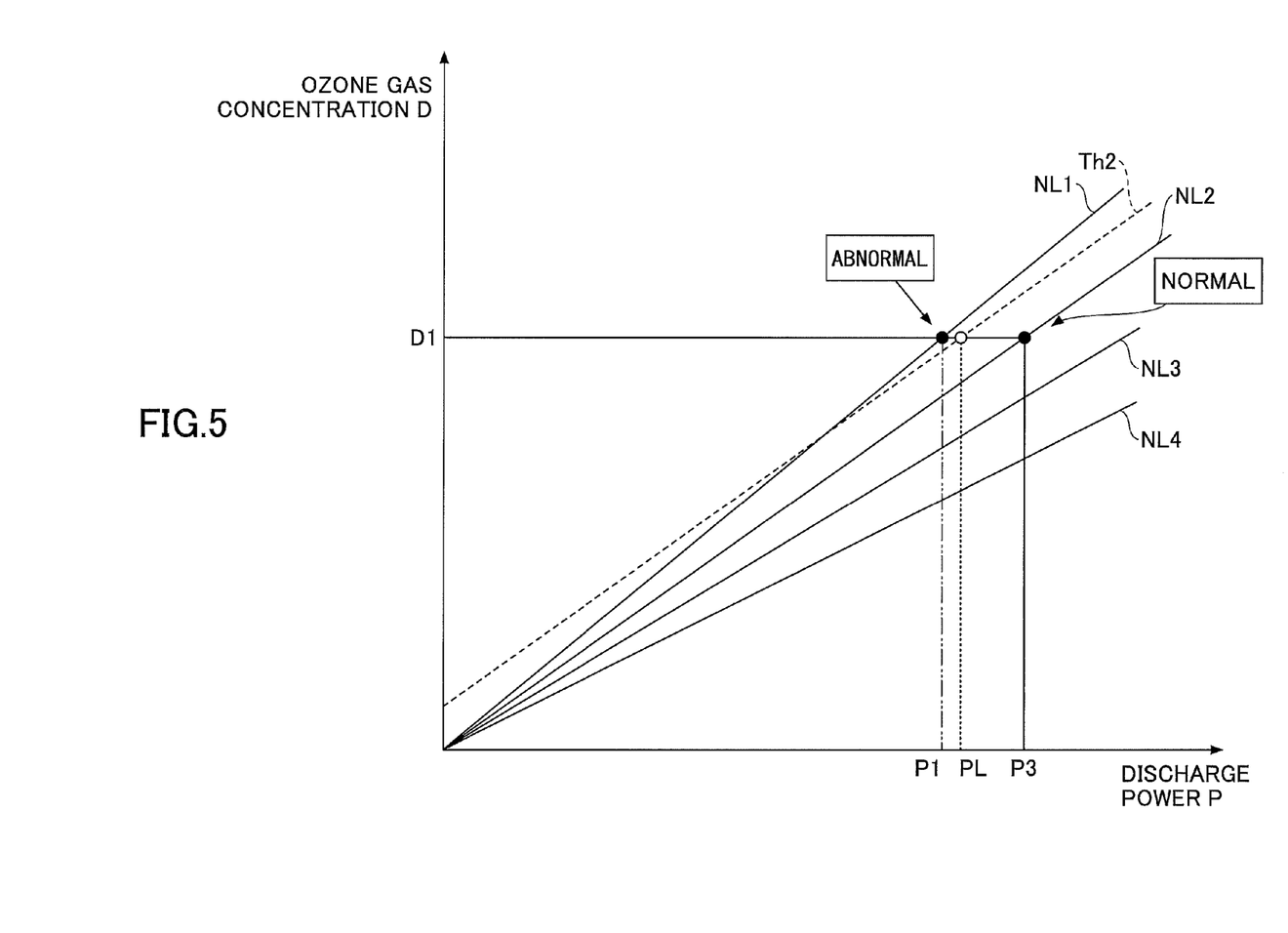
FIG. 5 is a chart illustrating an example of a graph illustrating a correlation between an ozone gas concentration and discharge power according to an embodiment of the present invention.

When the operating time of the ozonizer 22 does not pass over the time t1, the control unit 52 selects correlated information 1 (step S34). As illustrated in FIG. 5, the correlated information 1 shown by a straight line NL1 having the greatest slope is selected among straight lines NL1 through NL4 showing correlations of the ozone gas concentration and the discharge power. After the selection, the process of selecting the correlated information ends.

In contrast, when the operating time of the ozonizer 22 has passed over time t1, the control unit 52 determines whether the operating time of the ozonizer 22 has passed over predetermined time t2 (step S36).

When the operating time of the ozonizer 22 does not pass over time t2, the control unit 52 selects correlated information 2 from the memory unit 53 (step S38). As illustrated in FIG. 5, by doing this, correlated information 2 shown by a straight line NL2 having the second greatest slope is selected. After the selection, the process of selecting the correlated information ends.

On the other hand, when the operating time of the ozonizer 22 has passed over time t2, the control unit 52 determines whether the operating time of the ozonizer 22 has passed predetermined time t3 (step S40).

When the operating time of the ozonizer 22 does not pass over time t3, the control unit 52 selects correlated information 3 from the memory unit 53 (step S42). As illustrated in FIG. 5, by doing this, correlated information 3 shown by a straight line NL3 having the third greatest slope is selected. After the selection, the process of selecting the correlated information ends.

In contrast, when the operating time of the ozonizer 22 has passed time t3, the control unit 52 selects correlated information 4 from the memory unit 53 (step S44). By doing this, as illustrated in FIG. 5, correlated information 4 shown by a straight line NL4 having the smallest slope is selected. After the selection, the process of selecting the correlated information ends.

As discussed above, a description has been given of the modification of the embodiment. According to the modification, the most appropriate correlated information of the ozone gas concentration and the discharge power is selected depending on the temporal change of the ozonizer 22. This makes it possible to determine whether or not the ozone gas concentration is accurately measured with better accuracy based on the correlated information of the ozone gas concentration and the discharge power selected depending on the operating time of the ozonizer 22.

For example, when the operating time of the ozonizer 22 passes over time t1 but does not pass over time t2, if the operating time of the ozonizer 22 is not considered, the correlated information 1, in other words, presence or absence of the abnormality of the detected value of the ozone gas concentration is determined based on the straight line NL1 in FIG. 5. As a result, for example, when the monitored ozone gas concentration D is D1 and the discharge power P is P1, the discharge power P1 is a value on the straight line NL1, and the detected value of the ozone gas concentration detected by the ozone sensor 43 is determined to be normal.

On the other hand, in the modification, presence or absence of the abnormality of the detected value of the ozone gas concentration is determined based on the correlated information 2, in other words, the straight line NL2 in FIG. 5, depending on the operating time of the ozonizer 22. In this case, for example, when the monitored ozone gas concentration D is D1 and the discharge power P is P3, in the modification, based on the correlated information 2, it is determined that the detected discharge power P3 is a value on the straight line NL2, and that the ozone gas concentration is normal.

In contrast, when the monitored ozone gas concentration D is D1 and the discharge power P is P1, in the modification, based on the correlated information 2, the detected value of the ozone gas concentration is determined to be abnormal because the detected discharge power P1 is out of the range of PL to PH (which is not shown in FIG. 5).

In this manner, in the modification of the embodiment, whether or not the ozone gas concentration is accurately measured can be precisely determined based on the correlated information of the ozone gas concentration and the discharge power selected depending on the operating time of the ozonizer 22.

Hereinabove, although the substrate processing apparatus and the method for detecting the abnormality of the ozone gas concentration have been described according to the embodiments, the present invention is not limited to the embodiments and various modifications and improvements can be made without departing from the scope of the invention. Moreover, the embodiments and modifications can be combined as long as they are not contradictory to each other.

For example, the method for detecting the abnormality of the ozone gas concentration of the present invention is applicable to any system that monitors supply of ozone gas. Furthermore, the method of detecting the abnormality of the ozone gas concentration of the present invention is applicable to any system that monitors emissions of ozone gas.

For example, although not illustrated in FIG. 1, the ozone sensor 43 may be connected to the discharge pipe 31 that is connected to the ozone killer 41, and the ozone gas concentration within the exhaust gas sampled through the exhaust pipe 31 may be detected by using the ozone sensor 43. In this case, the method for detecting the abnormality of the ozone gas concentration of the present invention may determine whether or not the detected value of the ozone gas concentration is normal based on the ozone gas concentration and the discharge power by monitoring the ozone gas concentration within the exhaust gas and the discharge power by the monitor unit 51.

The substrate to be processed in the present invention is not limited to the wafer used in describing the embodiments, and for example, a large substrate for flat panel displays, a substrate for electroluminescence devices or a substrate for solar cells can be used instead.

As discussed above, according to the embodiments of the present invention, ozone gas can be reliably supplied by detecting an abnormality of an ozone gas concentration.

Here, the present invention is not limited to the configuration illustrated in the embodiments, but combining the configurations cited in the above embodiments with another component and the like are possible. In this regards, numerous variations and modifications are possible without departing from the scope of the present invention, and may be appropriately determined depending on such variations and modifications that may be made.

What is claimed is:

1. A substrate processing apparatus for processing a substrate by using ozone gas comprising:
   an ozonizer for generating ozone gas by using electrodes;
   an ozone sensor configured to detect an ozone gas concentration of the ozone gas generated by the ozonizer;
   a monitoring unit configured to monitor the ozone gas concentration detected by the ozone sensor and a discharge power that is electrical power output from the electrodes of the ozonizer; and
   a control unit configured to detect an abnormality of the ozone gas concentration based on the monitored ozone gas concentration and the monitored discharge power.

2. A substrate processing apparatus for processing a substrate by using ozone gas comprising:
   an ozonizer for generating ozone gas;
   an ozone sensor configured to detect an ozone gas concentration of the ozone gas generated by the ozonizer;

a monitoring unit configured to monitor the ozone gas concentration detected by the ozone sensor and a discharge power of the ozonizer;

a control unit configured to detect an abnormality of the ozone gas concentration based on the monitored ozone gas concentration and the monitored discharge power; and a memory unit storing correlated information showing a correlation between a second ozone gas concentration and a second discharge power, wherein the control unit detects the abnormality of the monitored ozone gas concentration in accordance with the correlated information showing the correlation between the second ozone gas concentration and the second discharge power stored in the memory unit, based on the monitored ozone gas concentration and the monitored discharge power.

3. The substrate processing apparatus as claimed in claim 2, wherein the control unit detects the abnormality of the monitored ozone gas concentration when the monitored discharge power corresponding to the monitored ozone gas concentration is out of a range of a predetermined acceptable value in accordance with the correlated information showing the second ozone gas concentration and the second discharge power stored in the memory unit.

4. The substrate processing apparatus as claimed in claim 2,
wherein the memory unit storing a plurality pieces of correlated information showing correlations between the second ozone gas concentration and the second discharge power that change depending on an operating period of time of the ozonizer, and wherein the control unit select any piece of correlated information among the plurality pieces of correlated information showing the correlations between the second ozone gas concentration and the second discharge power based on the measured operating period of time of the ozonizer, and detects the abnormality of the ozone gas concentration in accordance with the selected piece of correlated information.

5. A substrate processing apparatus for processing a substrate by using ozone gas comprising:
an ozonizer for generating ozone gas;
an ozone sensor configured to detect an ozone gas concentration of the ozone gas generated by the ozonizer;
a monitoring unit configured to monitor the ozone gas concentration detected by the ozone sensor and a discharge power of the ozonizer;
a control unit configured to detect an abnormality of the ozone gas concentration based on the monitored ozone gas concentration and the monitored discharge power; and
a chamber for processing the substrate therein,
wherein the ozone sensor is connected to a supply line for supplying the ozone gas from the ozonizer to the chamber.

6. A method for detecting an abnormality of an ozone gas concentration used in a substrate processing apparatus for processing a substrate by using an ozonizer for generating ozone gas by using electrodes, the method comprising:
monitoring an ozone gas concentration of the ozone gas supplied to the substrate processing apparatus, the ozone gas concentration being detected by an ozone sensor;
monitoring a discharge power that is electrical power output from the electrodes of the ozonizer; and
detecting an abnormality of the ozone gas concentration based on the monitored ozone gas concentration and the monitored discharge power.

* * * * *